(12) United States Patent
Basagañas Millan

(10) Patent No.: US 7,311,883 B2
(45) Date of Patent: Dec. 25, 2007

(54) SYSTEM FOR REGULATING EVAPORATION INTENSITY IN INSECTICIDAL FRESHENER DEVICES AND THE LIKE

(75) Inventor: Jordi Basagañas Millan, Barcelona (ES)

(73) Assignee: DBK Espana, S. A. (ES)

( * ) Notice: Subject to any disclaimer, the term of this patent is extended or adjusted under 35 U.S.C. 154(b) by 314 days.

(21) Appl. No.: 10/470,473

(22) PCT Filed: Jan. 29, 2001

(86) PCT No.: PCT/ES01/00018

§ 371 (c)(1),
(2), (4) Date: Sep. 2, 2003

(87) PCT Pub. No.: WO02/060494

PCT Pub. Date: Aug. 8, 2002

(65) Prior Publication Data

US 2004/0067173 A1    Apr. 8, 2004

(51) Int. Cl.
*A61L 9/03* (2006.01)
(52) U.S. Cl. .................. 422/125; 239/59; 392/392; 392/395
(58) Field of Classification Search ............. 422/125; 239/59, 58, 51.5; 392/387, 390, 394, 392, 392/395
See application file for complete search history.

(56) References Cited

U.S. PATENT DOCUMENTS

| | | | | |
|---|---|---|---|---|
| 472,133 A | * | 4/1892 | Merrill | 239/51.5 |
| 2,383,960 A | * | 9/1945 | Dupuy | 239/51.5 |
| 2,765,194 A | * | 10/1956 | Will | 239/59 |
| 3,848,803 A | * | 11/1974 | Levey | 239/59 |
| 3,872,280 A | * | 3/1975 | Van Dalen | 392/390 |
| 4,327,056 A | * | 4/1982 | Gaiser | 422/124 |
| 4,759,501 A | * | 7/1988 | Silvenis et al. | 239/6 |
| 4,968,487 A | | 11/1990 | Yamamoto et al. | 422/125 |
| 5,788,931 A | * | 8/1998 | Munoz Quintana | 422/125 |
| 6,254,248 B1 | * | 7/2001 | McAuley et al. | 362/101 |

FOREIGN PATENT DOCUMENTS

| | | |
|---|---|---|
| ES | 529718 | 1/1985 |
| ES | 2043621 | 1/1994 |
| ES | 2137111 | 12/1999 |
| WO | WO2000/76292 A2 * | 12/2000 |

* cited by examiner

Primary Examiner—E. Leigh McKane
(74) Attorney, Agent, or Firm—Ostrolenk, Faber, Gerb & Soffen, LLP

(57) ABSTRACT

The system is based on a change in the intensity of evaporation caused by a chimney effect, modifying the flow of air that circulates through the environment apparatus in the surrounding area of the wick. It consists of using a casing (1) with slots (6) for the passage of air in its upper part. This is done in such a manner that said casing (1) can be used in isolation, thus attaining an apparatus that does not regulate the evaporation intensity, but that has a complementary part (7) joined to the upper part of said casing (1). This assembly, enabling free turning, has complementary slots (9), that determine a greater or lesser flow of air and the consequent regulation of the intensity of the evaporation, depending on the greater or lesser degree of opposition they have to the slots (6).

5 Claims, 4 Drawing Sheets

SYSTEM FOR REGULATING EVAPORATION INTENSITY IN INSECTICIDAL FRESHENER DEVICES AND THE LIKE

OBJECT OF THE INVENTION

This invention refers to the field of insecticide or similar air-freshening apparatus, where a volatile product, of a nature appropriate for the objective sought in each case, is evaporated by means of the input of heat using one or more heating resistors, within a wick on which said resistors act, and that absorbs the product by capillary action from the corresponding container.

The object of the invention is to attain deliberate regulation, on the part of the user, of the intensity of evaporation of the product in question at all times.

BACKGROUND TO THE INVENTION

Evaporators of volatile substances are well-known. These are generally used as air-fresheners or insecticide elements that have a recipient container for the product in question. This product rises by capillary action through a wick that conveys the product in the direction of a heating resistor, in such a manner that the heat generated by the latter determines the evaporation product that is being used.

In order to adapt the use of these apparatus to different circumstances of use or the needs of the user, it is necessary for the rate of evaporation of the substances to be regulated, supplying the surrounding atmosphere with a greater or lesser quantity of evaporated product per unit of time.

In this respect the application for the Spanish Invention Patent ES-2.137.111 is well-known. This features one of these apparatus, in which the evaporation regulation rate is undertaken by varying the relative position between the wick and the heating element. The electro-heating resistors in this apparatus are maintained static. It is the container, along with the wick that is moved in an axial manner caused by the effect of a coil, in order to vary the degree of availability of the wick in the area of influence of the heating resistors.

Another solution is provided by our Spanish Invention Patent ES-2.163.956, in which the regulation of the degree of evaporation is carried out by means of a chimney effect, rather than by modifying the relative position between the wick and the heating resistors. By using an air current, this chimney effect causes the vaporised product to be dragged upwards, reinforcing the evaporation. To this end, use is made of a sleeve that is moved manually along a sliding guide bar on a sloping rail. The result is that said sleeve is made to take on the position of different heights. This in turn gives rise to different degrees of intensity in the said chimney effect, and accordingly to different rates of intensity in the evaporation of the product in question.

DESCRIPTION OF THE INVENTION

The evaporating apparatus with regulation of the intensity of evaporation that is proposed with the invention is based on the chimney effect that apparatus such as the one mentioned above feature. However, the apparatus proposed is based on a basic structure which makes correct operation possible, but that does not incorporate means for regulating the intensity of the evaporation. In order to achieve said evaporation intensity regulation, it is only necessary for a complementary part to be incorporated that converts said apparatus into one capable of controlling said regulation. On the other hand, if the function of acting on the evaporation intensity of the apparatus is not required, it will be sufficient not to attach said complementary part, or to remove it if it has already been placed in position. In this way, the apparatus will function normally and will not carry out any class of regulation on said evaporation intensity of the substance.

This means a drastic simplification from the manufacturing viewpoint. This is because while it is conventionally necessary to manufacture two completely different types of mechanisms or apparatus, one without the regulation function and the other with evaporation intensity regulation, with the system of this invention one single basic apparatus can be manufactured, that is equally valid in both the case in which regulation exists and if the aim is for there to be no regulation. When the objective is to obtain an apparatus that regulates evaporation intensity, it will be simply sufficient to attach the complementary part to said base apparatus.

In practice this is achieved by means of attaching a complementary part with coplanar slots or openings to the upper part of the casing of the apparatus. These can, to a greater or lesser extent, be set in opposition to the fixed slots or openings that appear in the upper part of the casing. This also limits the passage of the vapours through it, to a greater or lesser extent as appropriate. In this manner, the passage of the vapours from the inside of the casing to the outside can be regulated by means of a reduction or increase in the section through which said vapours gain access to the outside. As has been stated, this section is defined by the greater or lesser opposition of the coplanar slots of the complementary part and of the openings that are set in the casing.

Another possible form is the one in which the invention functions involving the casing incorporating a series of spurred indentations that surround the central opening through which the vapours rise, rather than the openings set in the upper part. In this other case, the complementary part has a cylindrical ring and axial, another series of spurred indentations that can to a greater or lesser extent be set in opposition to those of the casing. This complementary part can be joined by means of pressure to the upper base of the casing using strain-bearing teeth for instance, that will regulate the evaporation intensity on the basis of the angular position that it adopts with respect to the latter. This angular position will, to a greater or lesser extent, determine the degree of opposition between the fixed spurred slots and the moving spurred slots. In this way the variation or regulation of the chimney effect produced can be determined.

The apparatus can optionally incorporate the two types of slots, or slots with another configuration or disposition simultaneously.

DESCRIPTION OF THE DRAWINGS

In order to complement the description that is being made, and for the purpose of assisting greater understanding of the features of the invention, a series of drawings is attached as an integral part of said description so as to show the preferred example of the practical form of the same. These drawings have been represented in the following way, on an illustrative and non-limiting basis.

PREFERRED FORM OF THE INVENTION

Figure 1:
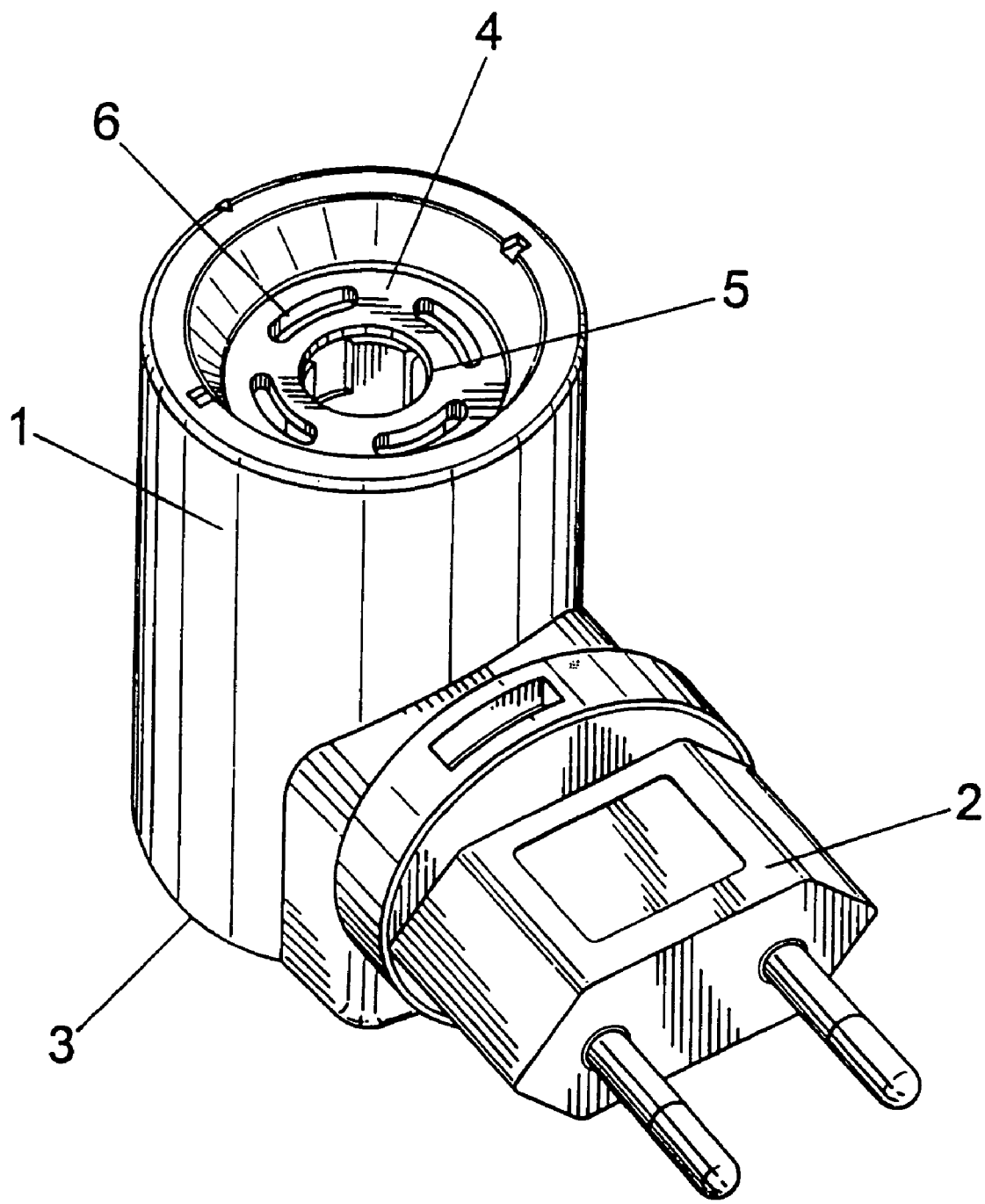
FIG. 1.—shows, from a perspective viewpoint, the casing corresponding to an air-freshening apparatus that is capable of including the evaporation intensity regulation system that constitutes the object of this invention.

In light of the figures described it is possible to observe how an airfreshening apparatus similar to the one that is applicable to the invention consists of a casing (1) which is extended by a connecting pin (2), in order to attach it to the plug base and the subsequent power supply of the electro-heating resistors set up inside the casing (1). This leads to the heating of the product which, being powered from a recipient that is not shown in the drawings that can be attached to the inner part of the casing (1), exits by capillary action along the typical wick on which the electro-heating resistors function.

Figure 3:
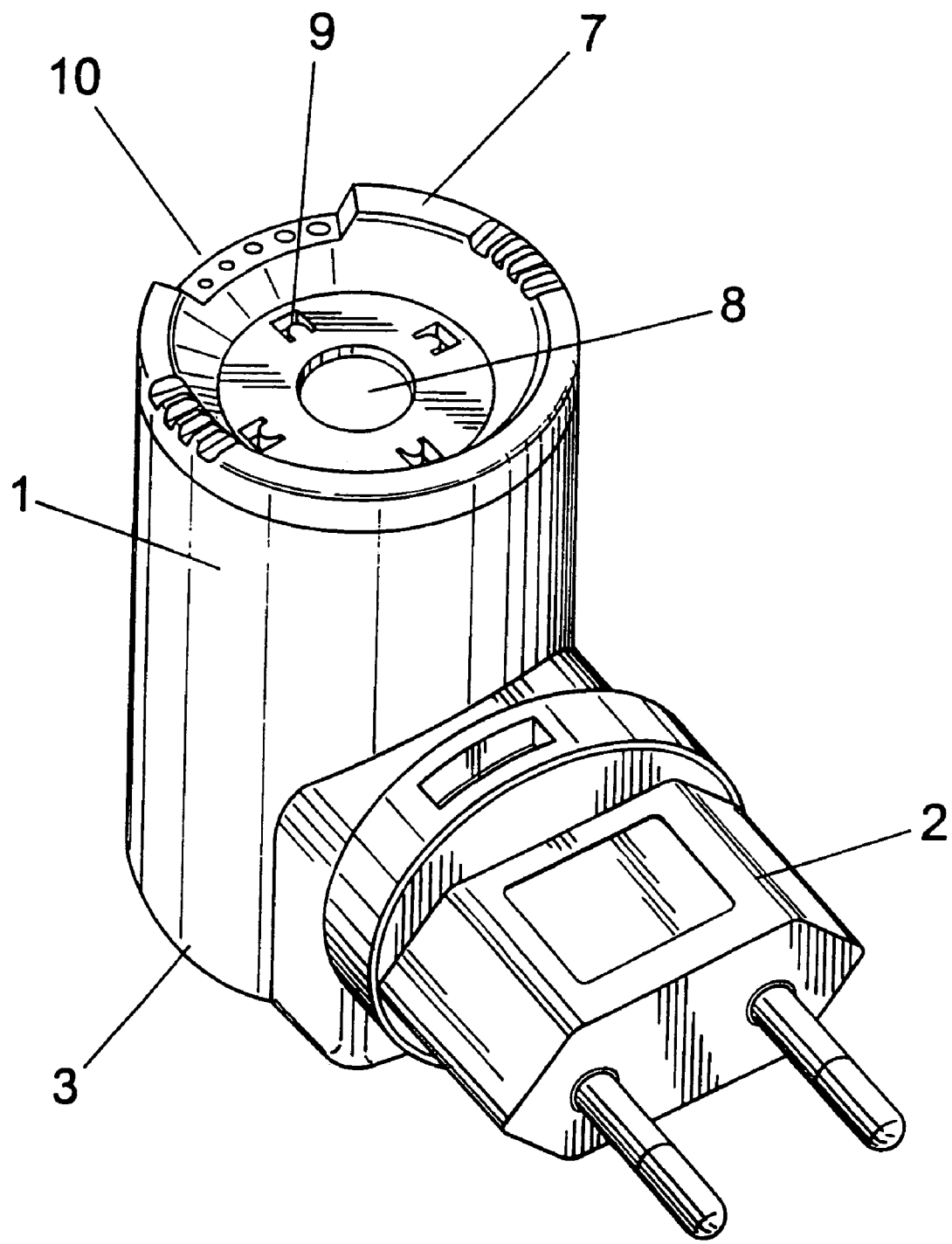
FIG. 3.—shows the apparatus from FIG. 1, following the attaching of the complementary part that converts it into an air-freshening apparatus with evaporation intensity regulation.

Hence, from this basic and conventional structuring and following the illustration of FIGS. 1 and 3, the apparatus of invention is based on the fact of the said casing (1) incorpores an axial opening (5) on the upper part of its base. This axial opening (5) is set in opposition to the wick cited, and the same is surrounded by a range of coplanar slots (6). In this practical form example, these slots (6) are configured as a circumference line. However, they may take the form of any other configuration or arrangement. This range, as shown in FIG. 1, is capable of functioning perfectly as an air-freshening or similar apparatus with a constant evaporation intensity rate; in other words, without the capability of regulating said intensity.

Said casing (1) is complemented by an auxiliary or complementary part (7), the one shown in FIG. 3. This is used by being attached to the upper part (4) of the casing (1) that has a cylindrical core (8) with flaps and pegging teeth in the opening (5) of the casing (1). Around said core (8) there are a set of coplanar openings (9) that can be set in opposition to the coplanar slots (6) of the casing (1) or not as the case may be. When this is done to a greater or lesser extent, it enables the said complementary part (7) to turn freely on the casing (1). This takes place in such a manner that a chimney effect is produced through the slots (6) and openings (9), that can be varied depending on the degree of opposition between them. This is clearly defined by means of a scale (10) that identifies the operational position of the complementary part (7) at any given moment.

Figure 2:
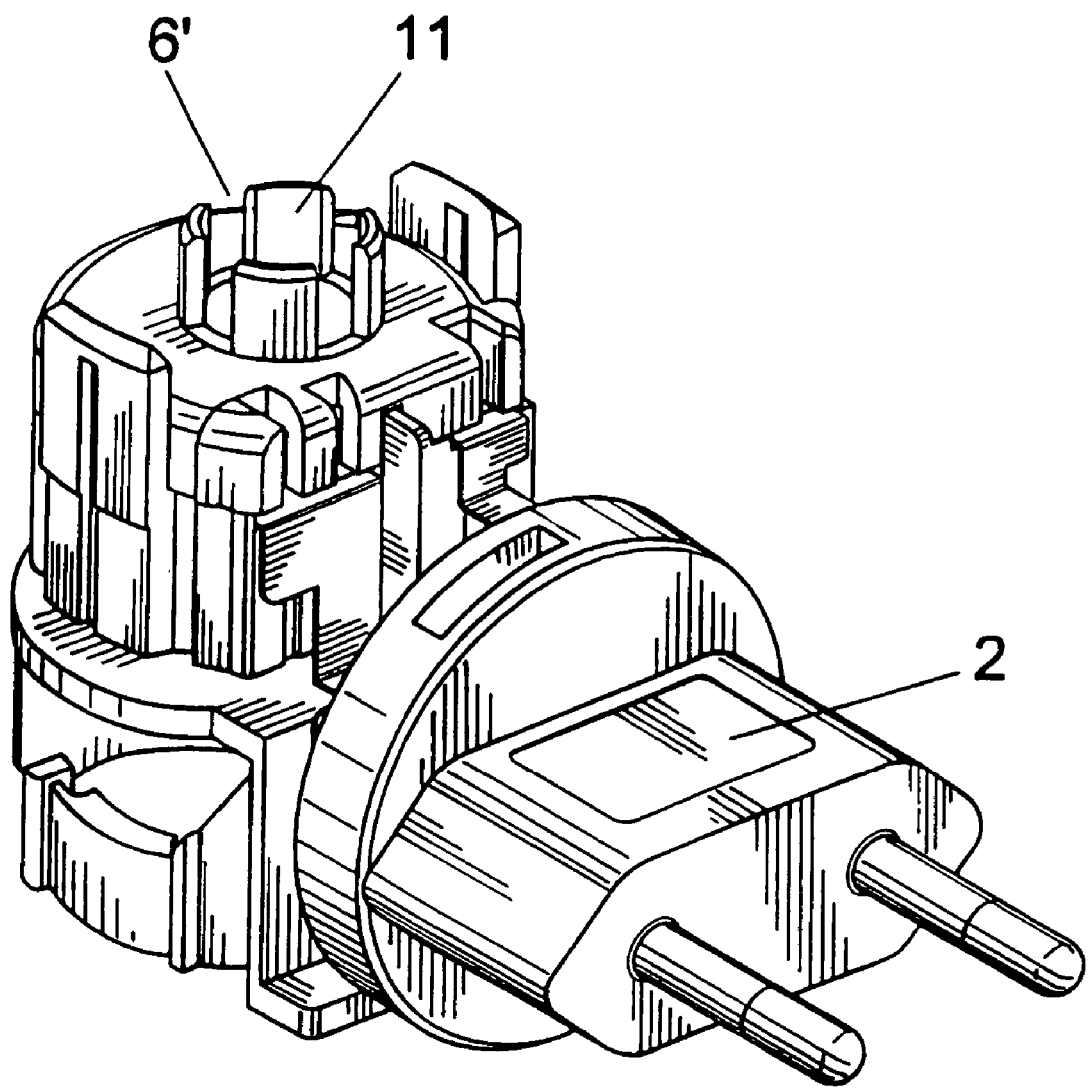
FIG. 2.—shows a variation on the form of the same casing from a similar perspective to that of the previous illustration.
Figure 4:
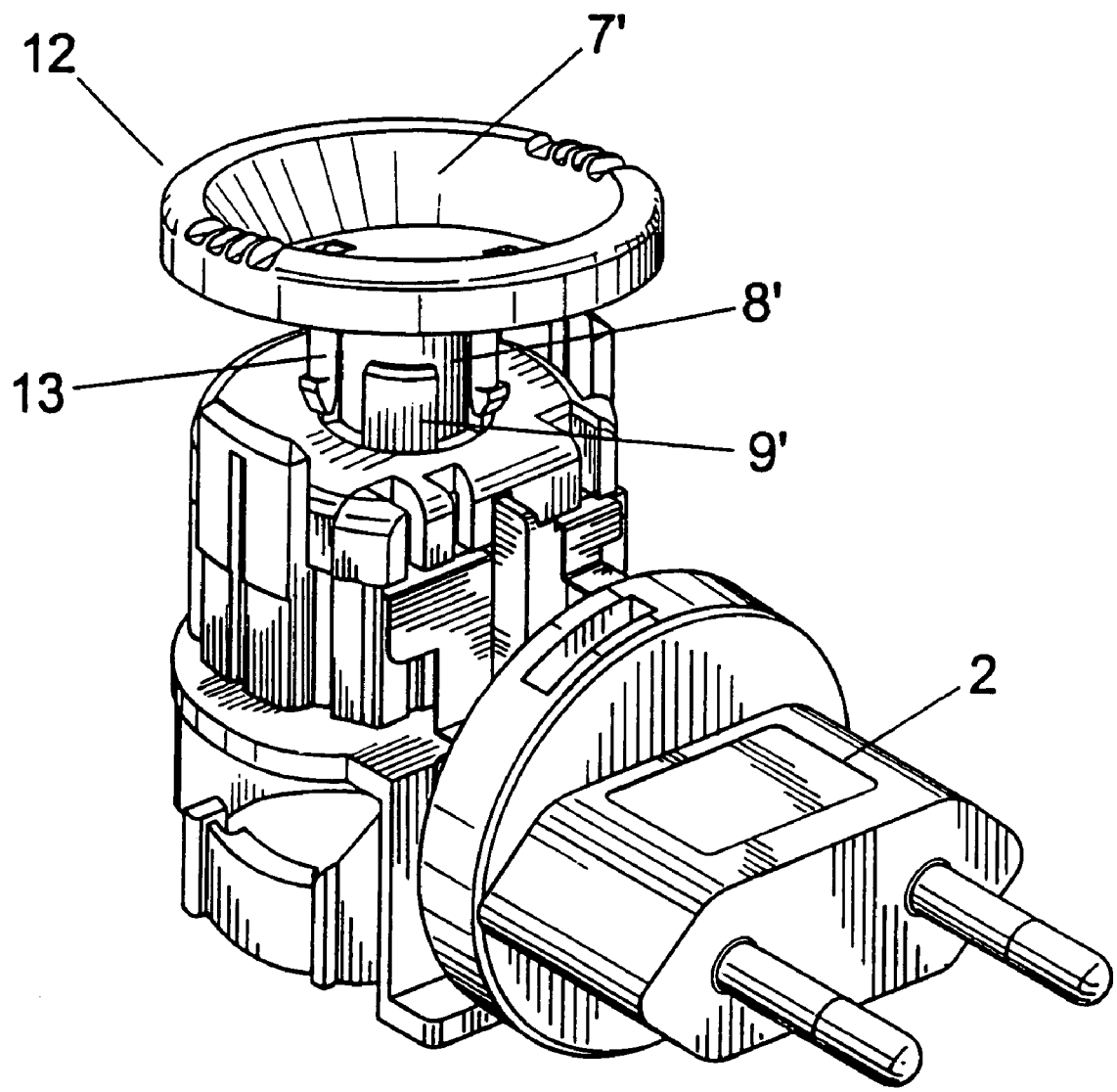
FIG. 4.—shows a similar representation to that in FIG. 3, but this one corresponds to the air-freshening apparatus of FIG. 2.

On an optional basis, and as shown in FIGS. 2 and 4, instead of the said coplanar slots (6), the casing (1) can include vertical slots (6'), that are set on a coaxial ring (11). This is done in such a manner that in this case, the complementary and regulatory part (7') that is incorporated into the core or ring (8') will also have, in addition to the same flaps (12) with pegging teeth (13) held by pressure on the opening of the unit or casing (1) that is not shown, moving vertical openings (9') that are complementary to the aforementioned slots (6'). These are connected in such a manner that, as in the previous case, the turning movement of the complementary part (7') determines the regulation of the evaporation intensity of the air-freshening product or the one in question, in relation to the casing (1).

As has also been mentioned above, there is the possibility of combining the two aforesaid solutions in such a way that the apparatus incorporates both vertical slots and openings (6'-9') and coplanar slots and openings (6-9).

In any event a situation is attained in which the apparatus can function as a conventional apparatus without the means of regulation, in the position of FIGS. 1 and 2, and without any kind of structural modification, but rather simply by means of the structural incorporation of the complementary part (7-7'), joined by means of pressure, to the casing (1). This converts the apparatus into a different one that is capable of permitting the deliberate regulation of the evaporation intensity that is produced by the same.

The invention claimed is:

1. Apparatus for evaporating volatile products in which evaporation occurs by means of a chimney effect, comprising:
    a casing and an evaporation intensity regulation system, wherein the evaporated product passes through windows or openings which section can be regulated by restriction of the passage of the same;
    wherein the casing further comprises a top surface including an axial opening positioned in opposition to a wick of the apparatus to allow for the flow of evaporated product through the axial opening and wherein the windows or openings are positioned around the axial opening and wherein the restriction of the passage of said windows or openings is carried out by means of a complementary part of the evaporation intensity regulation system mounted on said casing, wherein said complementary part incorporates openings that can be set in opposition in a greater or lesser extent to the windows or openings provided on said top surface of the casing so that the chimney effect is varied depending on the degree of opposition between the windows or openings of the casing and the openings of the complementary part in order to regulate the flow of evaporated product and consequently the intensity of evaporation; and
    a heating device mounted in the casing and operable to heat at least a portion of the wick.

2. Apparatus according to claim 1, wherein the windows or openings are positioned around the axial opening as coplanar slots formed in a common plane.

3. Apparatus according to claim 2, wherein the casing incorporates in its upper part vertical slots which can be set in opposition to moving vertical openings provided in a cylindrical ring of the complementary part to a greater or lesser extent, said complementary part being attachable to the upper part of the casing by pressure, wherein it can turn freely so that its angular position will, in a greater or lesser extent, determine the degree of opposition between the vertical slots and the moving vertical openings determining thereby the intensity of evaporation.

4. Apparatus according to claim 3, wherein the casing incorporates both the coplanar slots and vertical slots whereas the complementary part incorporates both the coplanar openings and moving vertical openings that operates in combination.

5. Apparatus according to claim 2, wherein the casing incorporates both the coplanar slots and vertical slots whereas the complementary part incorporates both coplanar openings and moving vertical openings that operates in combination.

* * * * *